United States Patent
Konerman et al.

(10) Patent No.: US 10,153,058 B2
(45) Date of Patent: Dec. 11, 2018

(54) MACHINE LEARNING FOR HEPATITIS C

(71) Applicant: THE REGENTS OF THE UNIVERSITY OF MICHIGAN, Ann Arbor, MI (US)

(72) Inventors: Monica A. Konerman, Ann Arbor, MI (US); Ulysses Balis, Ypsilanti, MI (US); Peter Higgins, Ann Arbor, MI (US); Ji Zhu, Ann Arbor, MI (US); Anna Lok, Ann Arbor, MI (US); Akbar Waljee, Ann Arbor, MI (US); Yiwei Zhang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 641 days.

(21) Appl. No.: 14/851,530

(22) Filed: Sep. 11, 2015

(65) Prior Publication Data
US 2016/0078184 A1 Mar. 17, 2016

Related U.S. Application Data

(60) Provisional application No. 62/049,027, filed on Sep. 11, 2014.

(51) Int. Cl.
| | |
|---|---|
| *G16H 50/20* | (2018.01) |
| *G06F 19/00* | (2018.01) |
| *G06N 99/00* | (2010.01) |
| *G06N 5/02* | (2006.01) |

(52) U.S. Cl.
CPC ............ *G16H 50/20* (2018.01); *G06F 19/00* (2013.01); *G06N 5/025* (2013.01); *G06N 99/005* (2013.01)

(58) Field of Classification Search
None
See application file for complete search history.

(56) References Cited

U.S. PATENT DOCUMENTS

| | | |
|---|---|---|
| 2002/0032384 A1 | 3/2002 | Raymond et al. |
| 2003/0228570 A1 | 12/2003 | Yat Wah Tom et al. |
| 2007/0208514 A1 | 9/2007 | Yatsuhashi et al. |
| 2007/0269804 A1* | 11/2007 | Liew .................. G06F 19/24 435/6.11 |

(Continued)

FOREIGN PATENT DOCUMENTS

WO WO-2014028888 A2 2/2014

OTHER PUBLICATIONS

Search Report for International application No. PCT/US2015/049570, dated Dec. 17, 2016.

(Continued)

*Primary Examiner* — Alan Chen
(74) *Attorney, Agent, or Firm* — Marshall, Gerstein & Borun LLP; Randall G. Rueth

(57) ABSTRACT

To predict which Hepatitis C patients are at high-risk for disease progression or adverse health outcomes, baseline characteristics are measured for patients as well as longitudinal data, including clinical, laboratory and/or biopsy results, which may be collected periodically in follow-up visits with a healthcare professional. A machine learning engine may predict whether a patient is at high-risk for disease progression or adverse health outcomes based on the baseline characteristics and the longitudinal data for the patient.

18 Claims, 6 Drawing Sheets

(56) References Cited

U.S. PATENT DOCUMENTS

| | | |
|---|---|---|
| 2011/0307426 A1 | 12/2011 | Syed et al. |
| 2013/0323720 A1* | 12/2013 | Watelet .............. C12Q 1/6883 435/5 |
| 2013/0325498 A1 | 12/2013 | Muza, Jr. et al. |
| 2014/0236621 A1 | 8/2014 | Six et al. |

OTHER PUBLICATIONS

Written Opinion for International application No. PCT/US2015/049570, dated Dec. 17, 2016.
Terrier B et al., "Prognostic factors in patients with hepatitis C virus infection and systemic vasculitis," Arthritis Rheum 63(6), pp. 1748-1757 (2011).
Hoshida Y et al., "Prognostic gene expression signature for patients with heptatis-C-related early-stage cirrhosis," Gastroenterology 144(5), pp. 1024-1030 (2013).
"HCV Guidance: Recommendations for Testing, Managing and Treating Hepatitis C," American Association for the Study of Liver Diseases, <http://www.hcvguidelines.org>.

* cited by examiner

| Risk Analysis For Disease Progression As A Result Of Hepatitis C ||| 500 |
|---|---|---|---|
| Patient Name | John Doe ←502 |||
| DOB | 03/05/1963 ←504 ||← 530|
|  | Clinical Decompensation Risk (%) || Fibrosis Progression Risk (%) |
| 1 years | 2.3 ←506 || 8.2 ←512 |
| 3 years | 5.7 ←508 || 12.6 ←514 |
| 5 years | 10.3 ←510 || 15.4 ←516 |
|  |  |  |  |

FIG. 5

MACHINE LEARNING FOR HEPATITIS C

CROSS-REFERENCE TO RELATED APPLICATIONS

This application claims priority to provisional U.S. Application Ser. No. 62/049,027, filed on Sep. 11, 2014, entitled "Machine Learning For Hepatitis C," the entire disclosure of which is hereby expressly incorporated by reference herein.

STATEMENT OF GOVERNMENTAL INTEREST

This invention was made with government support under T32DK062708 awarded by the National Institute of Health. The Government has certain rights in the invention.

TECHNICAL FIELD

The present application relates to health risk assessments and, more specifically, to a method and system for utilizing machine learning techniques to predict whether a patient is at high-risk for disease progression and/or adverse health outcomes.

BACKGROUND

According to "Sofosbuvir for Previously Untreated Chronic Hepatitis C Infection," by Lawitz et al., the continued advances in therapeutics for chronic hepatitis C (CHC) have dramatically altered the approach to treatment decision making given the marked improvement in efficacy and side effect profile of these agents. Whereas treatment would be deferred for many patients in the past given low efficacy and potential toxicity from therapy, presently a much larger pool of patients is being considered for treatment. There has simultaneously been a focus on improving screening and diagnosis of Hepatitis C virus (HCV) at the public health level. The major public health entities including the Centers for Disease Control and Prevention, the Institute of Medicine, and the United States Preventative Services Task Force have also advocated for treatment as a means of disease prevention.[1] The high prevalence of the disease paired with the significant cost of these new agents has created notable logistical and financial barriers to widespread treatment of patients with CHC.

[1] Moyer V A, Screening For Hepatitis C Virus Infection In Adults: U.S. Preventive Services Task Force Recommendation Statement. Ann Intern Med 2013.

SUMMARY

To identify disease progression in Hepatitis C patients, a health risk assessment system may be trained using various machine learning techniques to identify characteristics of patient data for a Hepatitis C patient, which may indicate that the patient will experience adverse health outcomes. The health risk assessment system may be trained by obtaining patient variables for several patients obtained at several points in time (also referred to herein as "training data"), where some of the patients experienced adverse health outcomes as a result of Hepatitis C while other patients did not experience any adverse health outcomes as a result of the virus. The training data may be analyzed using the various machine learning techniques to generate a statistical model which may be used to identify whether a patient with Hepatitis C is likely to experience adverse health outcomes in the future.

After the training period, the health risk assessment system may receive patient data, collected at several points in time, for a Hepatitis C patient where it is unknown whether the patient will experience adverse health outcomes (also referred to herein as an "unknown patient health status"). The patient data may be compared to the "learned" statistical model to determine a likelihood that the patient will experience adverse health outcomes as a result of Hepatitis C, which may be displayed on a health care provider's network-enabled device.

In this manner, health care providers may see which Hepatitis C patients are at high risk for experiencing adverse health outcomes, so that the health care providers can tailor preventative treatment to those patients who need it most. The present embodiments advantageously allow health care providers to accurately and efficiently identify Hepatitis C patients who are at high risk for experiencing adverse health outcomes. Moreover, by identifying these patients, the present embodiments advantageously ensure that high risk patients receive treatment preventing the onset of serious, debilitating complications, illnesses, or even death.

Furthermore, by distinguishing between Hepatitis C patients who are at high risk for cirrhosis complications and those who are not, the present embodiments advantageously allow for low risk patients to avoid treatment if they desire, reducing costs and the risk of potentially harmful side effects to the low risk patients. Finally, by accurately and efficiently identifying Hepatitis C patients who are at high risk for experiencing adverse health outcomes, the present embodiments may reduce costs to insurance providers. By reducing these costs, insurance providers may be more likely to provide coverage for the treatment, which may further increase the likelihood that a high risk patient will receive the treatment.

In an embodiment, a computer-implemented method for identifying disease progression in Hepatitis C patients is provided. The method includes obtaining a set of training data including a first subset having a first plurality of patient variables associated with a first set of patients having Hepatitis C who do not experience adverse health outcomes as a result of Hepatitis C and a second subset having a second plurality of patient variables associated with a second set of patients having Hepatitis C who do experience adverse health outcomes as a result of Hepatitis C. The method further includes receiving a set of patient data for a patient collected over a period of time, where the set of patient data includes a first plurality of patient characteristics collected at a first time and a second plurality of patient characteristics collected at a second time, comparing the set of patient data for the patient to the set of training data to determine a likelihood that the patient will experience adverse health outcomes as a result of Hepatitis C, and causing an indication of the likelihood that the patient will experience adverse health outcomes to be displayed on a user interface of a network-enabled device of a health care provider, where the health care provider recommends a course of treatment to the patient according to the determined likelihood.

In another embodiment, a computing device for identifying disease progression in Hepatitis C patients is provided. The computing device includes a communication network, one or more processors, and a non-transitory computer-readable memory coupled to the one or more processors and storing instructions thereon. When executed by the one or more processors, the instructions cause the system to obtain a set of training data including a first subset having a first plurality of patient variables associated with a first set of patients having Hepatitis C who do not experience adverse health outcomes as a result of Hepatitis C and a second subset having a second plurality of patient variables associated with a second set of patients having Hepatitis C who do experience adverse health outcomes as a result of Hepatitis. The instructions further cause the system to receive, via the communication network, a set of patient data for a patient collected over a period of time, where the set of patient data includes a first plurality of patient characteristics collected at a first time and a second plurality of patient characteristics collected at a second time, compare the set of patient data for the patient to the set of training data to determine a likelihood that the patient will experience adverse health outcomes as a result of Hepatitis C, and cause, via the communication network, an indication of the likelihood that the patient will experience adverse health outcomes to be displayed on a user interface of a network-enabled device of a health care provider, where the health care provider recommends a course of treatment to the patient according to the determined likelihood.

BRIEF DESCRIPTION OF THE DRAWINGS

FIG. 5 illustrates an exemplary risk analysis screen in accordance with the presently described embodiments.

DETAILED DESCRIPTION

Figure 1:
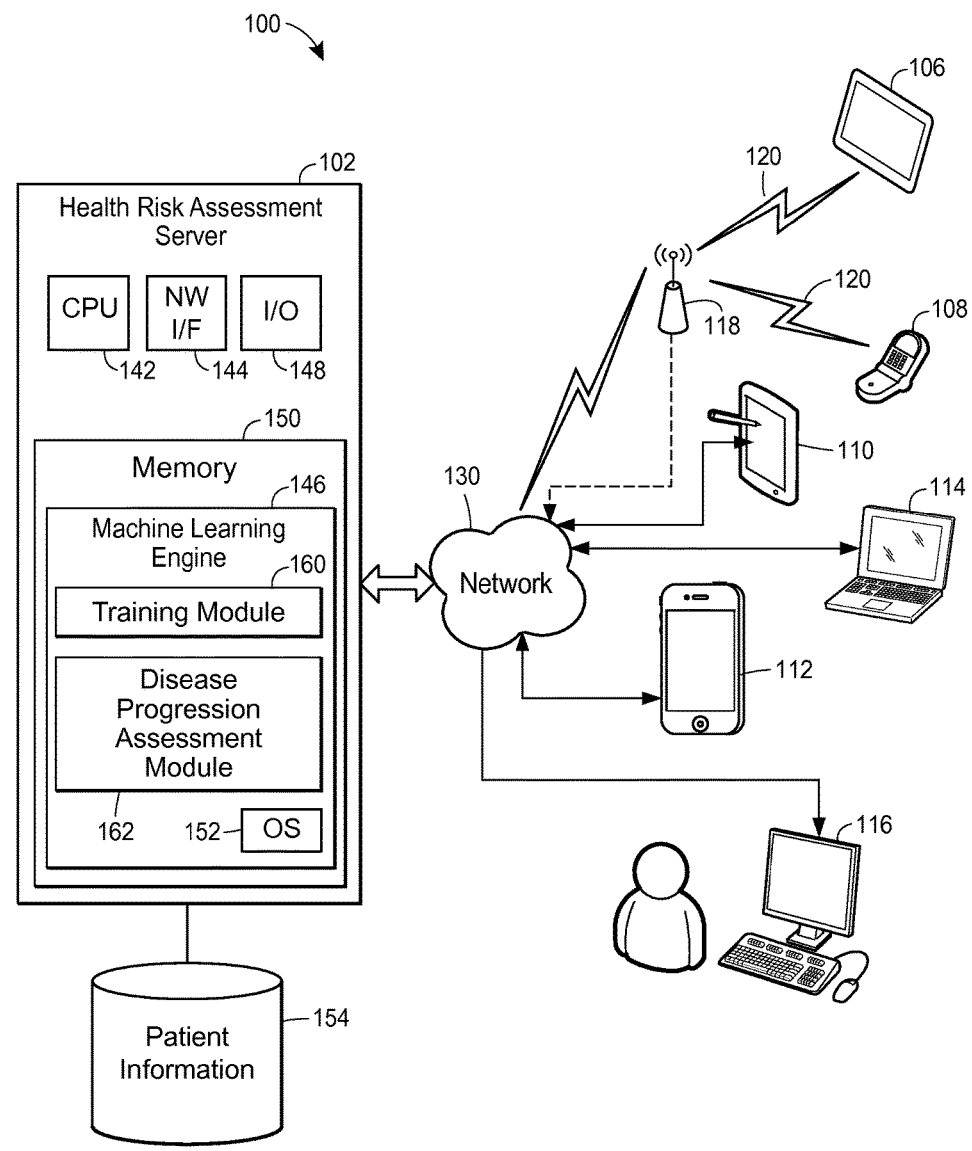
FIG. 1 illustrates a block diagram of a computer network and system on which an exemplary health risk assessment system may operate in accordance with the presently described embodiments.

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Accordingly, as used herein, the term "health care provider" may refer to any provider of medical or health services. For example, a health care provider may be a physician, nurse practitioner, physician assistant, etc.

As used herein, the term "patient variables" may refer to training data such as fixed characteristics, clinical variables, laboratory variables, and biopsy variables for Hepatitis C patients where it is known whether the patients experienced adverse health outcomes (also referred to herein as a "known patient health status"). For example, the Hepatitis C patients may have been infected for more than a predetermined amount of time (e.g., five years, ten years, etc.), and the patients may have been monitored to determine whether and/or when they experienced any adverse health outcomes from the infection.

On the other hand, the term "patient characteristics" as used herein, may refer to patient data for predicting whether a patient will experience adverse health outcomes as a result of having Hepatitis C. Patient characteristics may include fixed characteristics, clinical variables, laboratory variables, and biopsy variables for Hepatitis C patients where it is unknown whether the patients will experience an adverse health outcome (e.g., the patients have been infected for less than the predetermined amount of time).

As used herein, the term "adverse health outcomes" as a result of Hepatitis C may refer to any illnesses, complications, or death caused by the virus. For example, adverse health outcomes may include liver fibrosis progression, such as an increase in the patient's Ishak fibrosis score of two or more stages from the patient's baseline liver biopsy, liver-related death, liver decompensation, liver cancer, requiring a liver transplant, liver cirrhosis progression, such as an increase in the patient's Child-Turcotte-Pugh score of seven or more points, etc.

Generally speaking, techniques for identifying Hepatitis C patients at high risk for disease progression may be implemented in one or several network-enabled devices, one or several network servers, or a system that includes a combination of these devices. However, for clarity, the examples below focus primarily on an embodiment in which a health risk assessment server obtains a set of training data. In some embodiments, the training data may be obtained from a network-enabled device. The health risk assessment server may classify patient variables within the set of training data as one of: first patient variables associated with a set of first Hepatitis C patients who experienced adverse health outcomes or second patient variables associated with a second set of Hepatitis C patients who did not experience adverse health outcomes. The health risk assessment server may then be trained using the first and second patient variables to generate a statistical model for determining a likelihood that a patient will experience adverse health outcomes. Various machine learning techniques may be used to train the health risk assessment server.

After the health risk assessment server has been trained, patient data, collected at several points in time, may be received for a Hepatitis C patient where it is unknown whether she will experience adverse health outcomes. The patient data may include several patient characteristics, such as fixed characteristics, clinical variables, laboratory variables, and biopsy variables for identifying whether the patient will experience adverse health outcomes.

The patient data may then be analyzed, for example, using the various machine learning techniques to determine one or several likelihoods that the patient will experience adverse health outcomes within one or several predetermined amounts of time (e.g., one year, three years, five years, etc.). Indication(s) of the likelihood(s) may be transmitted to a health care provider's network-enabled device for the health care provider to review and determine an appropriate treatment plan or course of treatment based on the determined likelihood(s).

Referring to FIG. 1, an example health risk assessment system 100 includes a health risk assessment server 102 and a plurality of network-enabled device 106-116 which may be communicatively connected through a network 130, as described below. In an embodiment, the health risk assessment server 102 and the network-enabled devices 106-116 may communicate via wireless signals 120 over a digital network 130, which can be any suitable local or wide area network(s) including a Wi-Fi network, a Bluetooth network, a cellular network such as 3G, 4G, Long-Term Evolution (LTE), the Internet, etc. In some instances, the network-enabled devices 106-116 may communicate with the digital network 130 via an intervening wireless or wired device 118, which may be a wireless router, a wireless repeater, a base transceiver station of a mobile telephony provider, etc.

The network-enabled devices 106-116 may include, by way of example, a tablet computer 106, a network-enabled cell phone 108, a personal digital assistant (PDA) 110, a mobile device smart-phone 112 also referred to herein as a "mobile device," a laptop computer 114, a desktop computer 116, a portable media player (not shown), a wearable computing device such as Google Glass™ (not shown), a smart watch, a phablet, any device configured for wired or wireless RF (Radio Frequency) communication, etc. Moreover, any other suitable network-enabled device that records fixed characteristics, clinical variables, laboratory variables, or biopsy variables for patients may also communicate with the health risk assessment server 102.

Each of the network-enabled devices 106-116 may interact with the health risk assessment server 102 to transmit the fixed characteristics, clinical variables, laboratory variables, or biopsy variables which may be collected at baseline (when the patient first agrees to have his risk assessed or when the patient is initially diagnosed with Hepatitis C) and/or may be collected periodically at one or several follow-up visits (e.g., every three months, every six months, every two years, every three years, etc.).

Each network-enabled device 106-116 may also interact with the health risk assessment server 102 to receive one or several indication(s) of a likelihood(s) that a Hepatitis C patient will experience adverse health outcomes. For example, adverse health outcomes may include but are not limited to, liver fibrosis progression, such as an increase in the patient's Ishak fibrosis score of two or more stages from the patient's baseline liver biopsy, liver-related death, liver decompensation, liver cancer, requiring a liver transplant, liver cirrhosis progression, such as an increase in the patient's Child-Turcotte-Pugh score of seven or more points, etc.

In an example implementation, the health risk assessment server 102 may be a cloud based server, an application server, a web server, etc., and includes a memory 150, one or more processors (CPU) 142 such as a microprocessor coupled to the memory 150, a network interface unit 144, and an I/O module 148 which may be a keyboard or a touchscreen, for example.

The health risk assessment server 102 may also be communicatively connected to a patient information database 154. The patient information database 154 may store the fixed characteristics, clinical variables, laboratory variables, and biopsy variables collected at baseline or during previous follow-up visits for each patient. In some embodiments, to determine a likelihood that a Hepatitis C patient will experience adverse health outcomes, the health risk assessment server 102 may retrieve patient information for each patient from the patient information database 154.

The memory 150 may be tangible, non-transitory memory and may include any types of suitable memory modules, including random access memory (RAM), read only memory (ROM), flash memory, other types of persistent memory, etc. The memory 150 may store, for example instructions executable of the processors 142 for an operating system (OS) 152 which may be any type of suitable operating system such as modern smartphone operating systems, for example. The memory 150 may also store, for example instructions executable on the processors 142 for a machine learning engine 146 which may include a training module 160 and a disease progression assessment module 162. The health risk assessment server 102 is described in more detail below with reference to FIG. 2A. In some embodiments, the machine learning engine 146 may be a part of one or more of the network-enabled devices 106-116, the health risk assessment server 102, or a combination of the health risk assessment server 140 and the network-enabled devices 106-116.

In any event, the machine learning engine 146 may receive electronic data from the network-enabled devices 106-116. For example, the machine learning engine 146 may obtain a set of training data by receiving fixed characteristics, clinical variables, laboratory variables, and/or biopsy variables, collected at baseline and/or at one or more follow-up visits, for Hepatitis C patients who experienced adverse health outcomes and for Hepatitis C patients who did not experience any adverse health outcomes after being diagnosed with the virus for more than a predetermined amount of time (e.g., three years, five years, etc.). The fixed characteristics, clinical variables, laboratory variables, and/or biopsy variables may be received from healthcare professionals, for example on a desktop computer 116 which may transmit the set of training data to the health risk assessment server 102.

As a result, the training module 160 may classify the patient variables as corresponding to either patients who experienced adverse health outcomes or patients who did not experience adverse health outcomes, and/or the patient variables may be classified into specific types of adverse health outcomes, such as fibrosis progression, liver decompensation, liver cancer, requiring a liver transplant, etc. The training module 160 may then analyze the classified patient variables to generate a statistical model for determining a likelihood that a Hepatitis C patient will experience an adverse health outcome.

In some embodiments, the training module 160 may generate a statistical model for each adverse health outcome. For example, a first statistical model may be generated for determining a likelihood that a Hepatitis C patient will experience fibrosis progression, a second statistical model may be generated for determining a likelihood that a Hepatitis C patient will require a liver transplant, a third statistical model may be generated for determining a likelihood that a Hepatitis C patient will develop liver cancer, etc. In any event, the set of training data may be analyzed using various machine learning techniques, such as random forests and boosting. In a testing phase, the training module 160 may compare test patient data for a test patient to the statistical model to determine a likelihood that the test patient will experience adverse health outcomes.

If the training module 160 makes the correct determination more frequently than a predetermined threshold amount, the statistical model may be provided to a disease progression assessment module 162. On the other hand, if the training module 160 does not make the correct determination more frequently than the predetermined threshold amount, the training module 160 may continue to obtain training data for further training.

The disease progression assessment module 162 may obtain the statistical model as well as a set of patient data for a Hepatitis C patient, which may be collected over a period of time (e.g., six months, one year, three years, seven years, etc.). For example, a healthcare professional may input clinical, laboratory, and/or biopsy results, collected at baseline or during one or several follow-up visits for a patient on a desktop computer 116 which may be transmitted to the health risk assessment server 102. The disease progression assessment module 162 may then analyze the clinical, laboratory, and/or biopsy results, for example to determine a baseline, a mean, a maximum, an average slope, a maximum slope, and an acceleration for a patient characteristic collected at several points in time, such as a complete blood count for the patient.

The analyzed results may then be compared to the statistical model. Based on the comparison, the disease progression assessment module 162 may determine a likelihood that the patient will experience adverse health outcomes, and may cause the likelihood to be displayed on a user interface for a health care provider to review. Each likelihood may be represented as a probability (e.g., 0.6), a percentage (e.g., 80 percent), a category from a set of categories (e.g., "High," "Medium," or "Low"), and/or in any other suitable manner.

The health risk assessment server 102 may communicate with the network-enabled devices 106-116 via the network 130. The digital network 130 may be a proprietary network, a secure public Internet, a virtual private network and/or some other type of network, such as dedicated access lines, plain ordinary telephone lines, satellite links, combinations of these, etc. Where the digital network 130 comprises the Internet, data communication may take place over the digital network 130 via an Internet communication protocol.

Figure 2A:
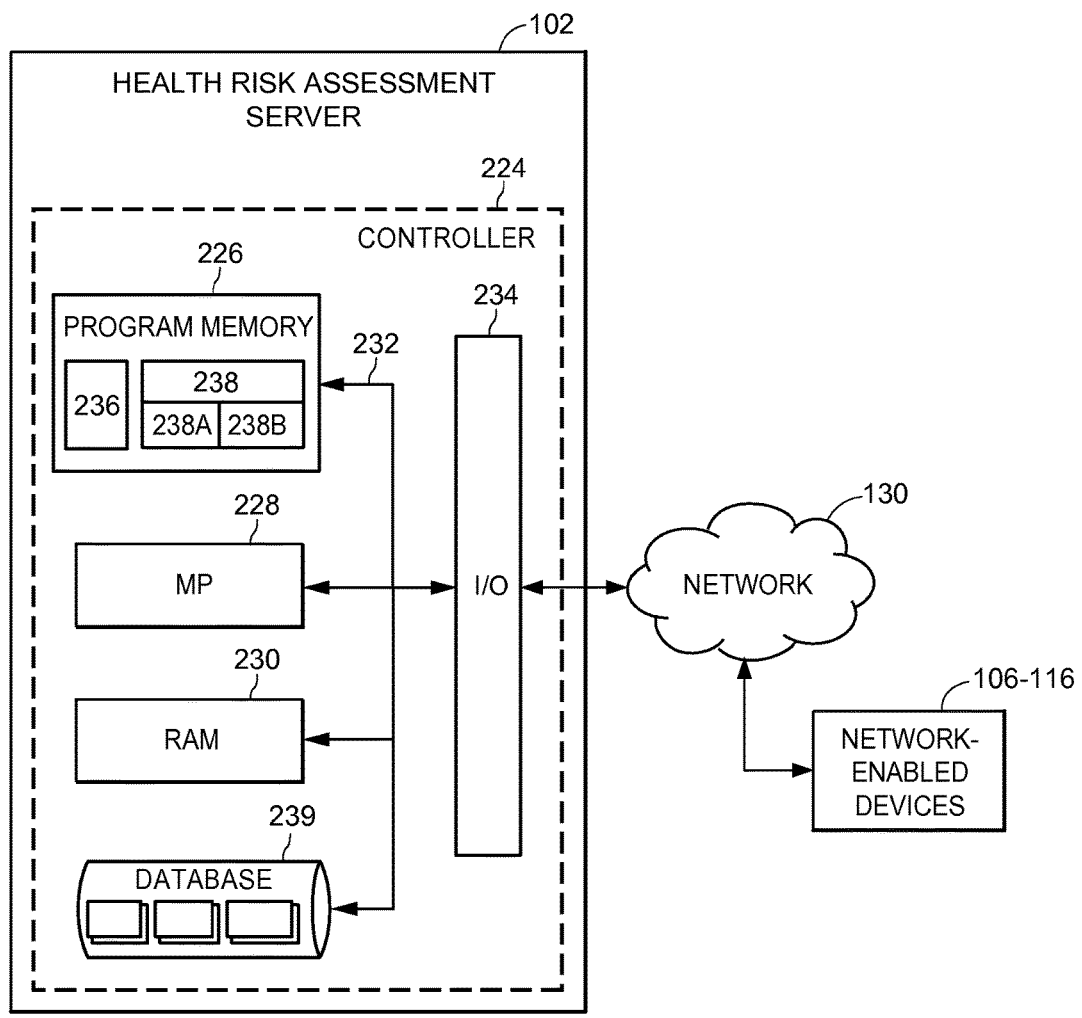
FIG. 2A is a block diagram of an exemplary health risk assessment server that can operate in the system of FIG. 1 in accordance with the presently described embodiments.

Turning now to FIG. 2A, the health risk assessment server 102 may include a controller 224. The controller 224 may include a program memory 226, a microcontroller or a microprocessor (MP) 228, a random-access memory (RAM) 230, and/or an input/output (I/O) circuit 234, all of which may be interconnected via an address/data bus 232. In some embodiments, the controller 224 may also include, or otherwise be communicatively connected to, a database 239 or other data storage mechanism (e.g., one or more hard disk drives, optical storage drives, solid state storage devices, etc.). The database 239 may include data such as patient information, training data, risk analysis templates, web page templates and/or web pages, and other data necessary to interact with users through the network 130. It should be appreciated that although FIG. 2A depicts only one microprocessor 228, the controller 224 may include multiple microprocessors 228. Similarly, the memory of the controller 224 may include multiple RAMs 230 and/or multiple program memories 226. Although FIG. 2A depicts the I/O circuit 234 as a single block, the I/O circuit 234 may include a number of different types of I/O circuits. The controller 224 may implement the RAM(s) 230 and/or the program memories 226 as semiconductor memories, magnetically readable memories, and/or optically readable memories, for example.

As shown in FIG. 2A, the program memory 226 and/or the RAM 230 may store various applications for execution by the microprocessor 228. For example, a user-interface application 236 may provide a user interface to the health risk assessment server 102, which user interface may, for example, allow a system administrator to configure, troubleshoot, or test various aspects of the server's operation. A server application 238 may operate to receive a set of patient data for a Hepatitis C patient, determine a likelihood that the Hepatitis C patient will experience adverse health outcomes, and transmit an indication of the likelihood to a health care provider's network-enabled device 106-116. The server application 238 may be a single module 238 or a plurality of modules 238A, 238B such as the training module 160 and the disease progression assessment module 162.

While the server application 238 is depicted in FIG. 2A as including two modules, 238A and 238B, the server application 238 may include any number of modules accomplishing tasks related to implementation of the health risk assessment server 102. Moreover, it will be appreciated that although only one health risk assessment server 102 is depicted in FIG. 2A, multiple health risk assessment servers 102 may be provided for the purpose of distributing server load, serving different web pages, etc. These multiple health risk assessment servers 102 may include a web server, an entity-specific server (e.g. an Apple® server, etc.), a server that is disposed in a retail or proprietary network, etc.

Figure 2B:
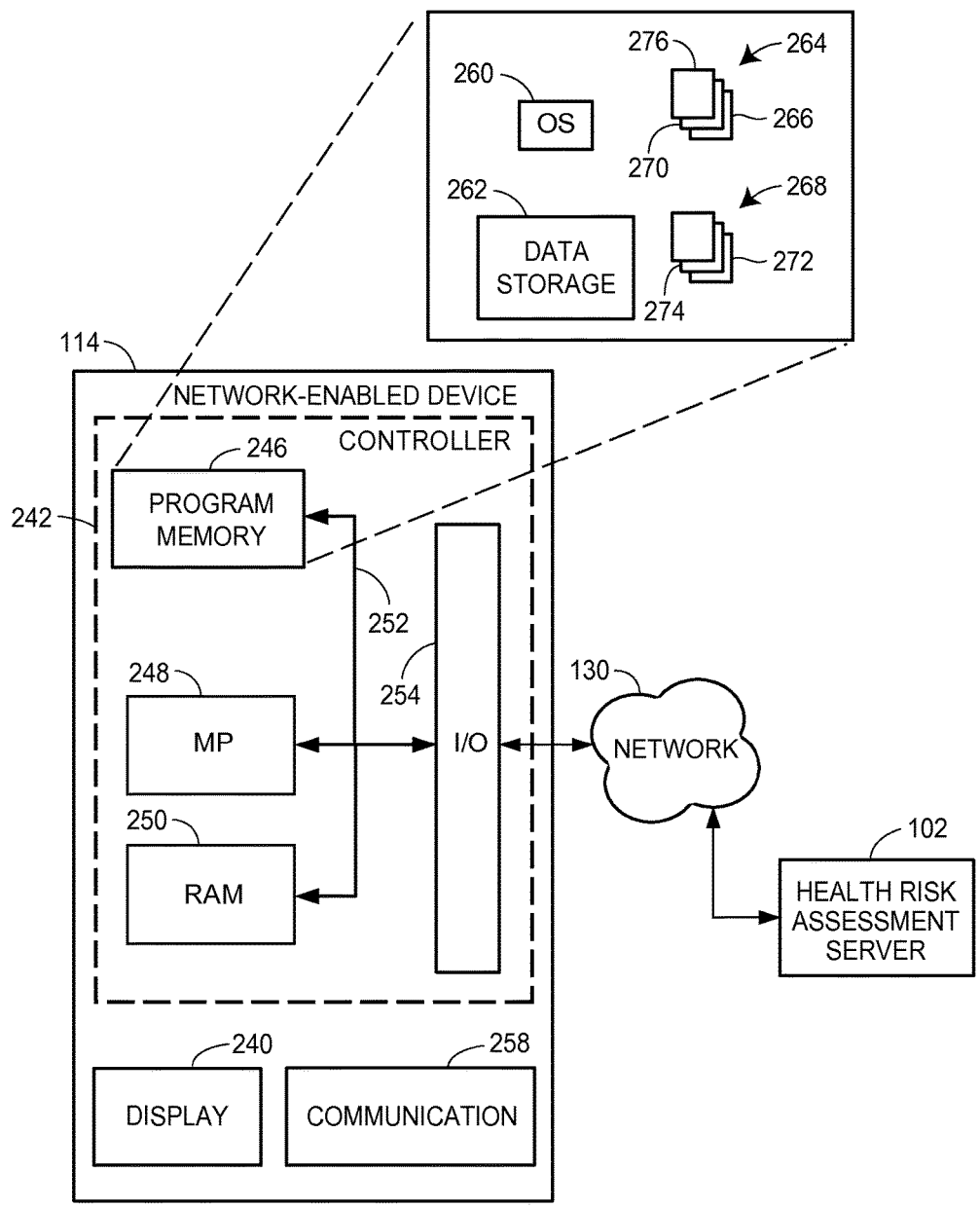
FIG. 2B is a block diagram of an exemplary network-enabled device that can operate in the system of FIG. 1 in accordance with the presently described embodiments.

Referring now to FIG. 2B, the laptop computer 114 (or any of the network-enabled devices 106-116) may include a display 240, a communication unit 258, a user-input device (not shown), and, like the health risk assessment server 102, a controller 242. Similar to the controller 224, the controller 242 may include a program memory 246, a microcontroller or a microprocessor (MP) 248, a random-access memory (RAM) 250, and/or an input/output (I/O) circuit 254, all of which may be interconnected via an address/data bus 252. The program memory 246 may include an operating system 260, a data storage 262, a plurality of software applications 264, and/or a plurality of software routines 268. The operating system 260, for example, may include Microsoft Windows®, OS X®, Linux®, Unix®, etc. The data storage 262 may include data such as patient information, application data for the plurality of applications 264, routine data for the plurality of routines 268, and/or other data necessary to interact with the health risk assessment server 102 through the digital network 130. In some embodiments, the controller 242 may also include, or otherwise be communicatively connected to, other data storage mechanisms (e.g., one or more hard disk drives, optical storage drives, solid state storage devices, etc.) that reside within the laptop computer 114.

The communication unit 258 may communicate with the health risk assessment server 102 via any suitable wireless communication protocol network, such as a wireless telephony network (e.g., GSM, CDMA, LTE, etc.), a Wi-Fi network (802.11 standards), a WiMAX network, a Bluetooth network, etc. The user-input device (not shown) may include a "soft" keyboard that is displayed on the display 240 of the laptop computer 114, an external hardware keyboard communicating via a wired or a wireless connection (e.g., a Bluetooth keyboard), an external mouse, a microphone for receiving voice input or any other suitable user-input device. As discussed with reference to the controller 224, it should be appreciated that although FIG. 2B depicts only one microprocessor 248, the controller 242 may include multiple microprocessors 248. Similarly, the memory of the controller 242 may include multiple RAMs 250 and/or multiple program memories 246. Although the FIG. 2B depicts the I/O circuit 254 as a single block, the I/O circuit 254 may include a number of different types of I/O circuits. The controller 242 may implement the RAM(s) 250 and/or the program memories 246 as semiconductor memories, magnetically readable memories, and/or optically readable memories, for example.

The one or more processors 248 may be adapted and configured to execute any one or more of the plurality of software applications 264 and/or any one or more of the plurality of software routines 268 residing in the program memory 246, in addition to other software applications. One of the plurality of applications 264 may be a client application 266 that may be implemented as a series of machine-readable instructions for performing the various tasks associated with receiving information at, displaying information on, and/or transmitting information from the laptop computer 114.

One of the plurality of applications 264 may be a native application and/or web browser 270, such as Apple's Safari®, Google Chrome™, Microsoft Internet Explorer®, and Mozilla Firefox® that may be implemented as a series of machine-readable instructions for receiving, interpreting, and/or displaying web page information from the health risk assessment server 102 while also receiving inputs from a user such as a health care provider. Another application of the plurality of applications may include an embedded web browser 276 that may be implemented as a series of machine-readable instructions for receiving, interpreting, and/or displaying web page information from the health risk assessment server 102.

One of the plurality of routines may include a risk analysis display routine 272 which obtains a likelihood that the Hepatitis C patient will experience adverse health outcomes and displays the likelihood on the display 240. Another routine in the plurality of routines may include a data entry routine 274 which obtains patient data for a patient from the health care provider and transmits the received patient data along with previously stored patient data for the patient (e.g., baseline patient data or patient data collected at a previous follow-up visit) to the health risk assessment server 102.

Preferably, a user may launch the client application 266 from a network-enabled device, such as one of the network-enabled devices 106-116 to communicate with the health risk assessment server 102 to implement the health risk assessment system 100. Additionally, the user may also launch or instantiate any other suitable user interface application (e.g., the native application or web browser 270, or any other one of the plurality of software applications 264) to access the health risk assessment server 102 to realize the health risk assessment system 100.

Figure 3:
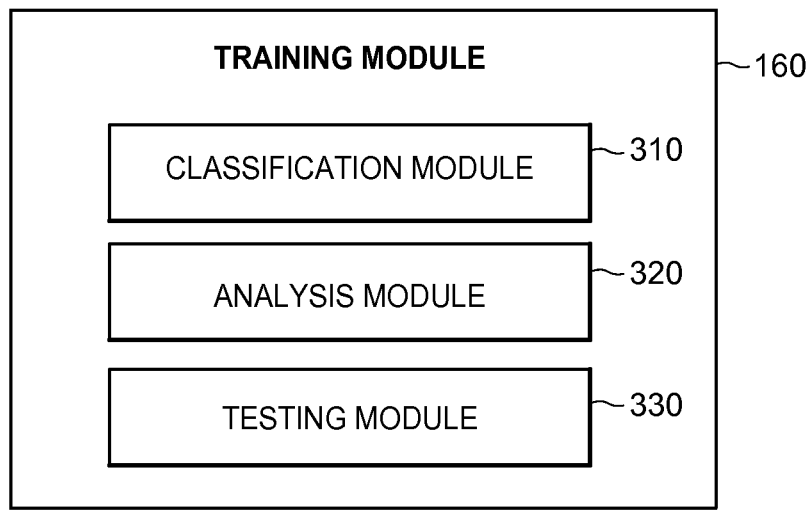
FIG. 3 depicts an exemplary training module in accordance with the presently described embodiments.

As mentioned above, the health risk assessment server 102 as shown in FIG. 1, may include a memory 150 which may store instructions executable on the processors 142 for a machine learning engine 146. The machine learning engine 146 may include a training module 160 and a disease progression assessment module 162. FIG. 3 is an exemplary block diagram of the training module 160. The training module 160 may include a classification module 310, an analysis module 320, and a testing module 330.

The training module 160 may obtain, for example from the network-enabled devices 106-116, a set of training data which may include several patient variables for several Hepatitis C patients where it is known whether the patients experienced adverse health outcomes. The patient variables may include fixed characteristics, clinical variables, laboratory variables, and biopsy variables.

More specifically, fixed characteristics may include patient demographics such as age, gender, nationality, etc. Fixed characteristics may also include Hepatitis C virus (HCV) genotype, IL28B genotype, history of alcohol and tobacco use, history of diabetes, estimated duration of HCV infection, etc. Clinical variables may include body mass index (BMI), waist circumference, an amount of beta-blocker use, an amount of anti-hypertensive use, evidence of portal hypertension, an average amount of alcohol consumed per day, etc. Laboratory variables may include HCV ribonucleic acid (RNA) level, complete blood count (CBC) with differential, comprehensive metabolic panel (CMP) results, alpha-fetoprotein (AFP) level, prothrombin time/international normalized ratio (INR), model of end-stage liver disease (MELD) score, aspartate aminotransferase (AST) to platelet ratio index (APRI), triglyceride (TG) level, insulin level, insulin resistance index (HOMA2IR), results from iron studies, ferritin level, Child-Turcotte-Pugh (CTP) score, etc. Biopsy variables may include Ishak score, histologic activity index (HAI), degree of steatosis, iron content, etc.

Each of these patient variables may be obtained at several points in time for each patient. For example, a BMI for patient Bob Smith may first be obtained at baseline (when he is first diagnosed with Hepatitis C), may be obtained a second time at a follow-up visit three months later, and a third time at another follow-up visit two years later. Moreover, the training module 160 may collect data each time for the same type of patient variable (BMI) for a patient and calculate several statistical measures, such as a baseline, a mean, a maximum, a mean slope, a maximum slope, and an acceleration.

For example, if a Hepatitis C patient's BMI is 25 at baseline, 22 at a first follow-up visit, and 19 at a second follow-up visit, the baseline may be 25, the mean may be 22, the maximum may be 25, the mean slope may be the average slope of a line or curve fit to the data set based on the difference in the patient's BMI at each point in time, the maximum slope may be the highest slope of a line or curve fit to the data set, and the acceleration may be the slope of the slope of a line or curve fit to the data set. For example, in some embodiments, the mean slope may be calculated based on the change in BMI divided by the change in time. The mean slope may be calculated based on the average slope of a best fit line which approximates the BMIs as a function of time. However, in other embodiments a best fit curve may be generated which is the closest approximation to the BMIs as a function of time. The best fit curve may be polynomial, logarithmic, exponential, etc. In such an embodiment, the mean slope may be calculated as the average slope of the best fit curve which approximates the patient's BMI as a function of time.

In any event, the classification module 310 may classify each of these patient variables and/or statistical measures for each patient into one of a first subset of the training data corresponding to Hepatitis C patients who did not experience adverse health outcomes or a second subset of the training data corresponding to Hepatitis C patients who experienced adverse health outcomes.

In some embodiments, the classification module 310 may classify each of these statistical measures based on whether the statistical measure corresponds to a patient who experienced a particular adverse health outcome, such as fibrosis progression, liver-related death, liver decompensation, liver cancer, requiring a liver transplant, liver cirrhosis progression, etc. In such an embodiment, the training module 160 may generate different statistical models for determining a likelihood that a Hepatitis C patient will experience each adverse outcome. In other embodiments, the training module 160 may generate a single statistical model for determining a likelihood that a Hepatitis C patient will experience any of the adverse health outcomes, or may generate any number of statistical models for determining a likelihood that a Hepatitis C patient will experience any number of the adverse health outcomes.

In any event, for each patient, the classification module 310 may obtain an indication of whether the patient experienced any adverse health outcomes and if so, the classification module 310 may obtain indications of which adverse health outcomes the patient experienced. As a result, the classification module 310 may classify each of the patient variables and/or statistical measures corresponding to the patient, accordingly. For example, if Hepatitis C patient Jane Anderson experienced fibrosis progression, the classification module 310 may classify each of her baseline APRI, mean APRI, maximum APRI, mean APRI slope, maximum APRI slope, and APRI acceleration as corresponding to a patient who experienced fibrosis progression. Additionally, statistical measures for each of her other patient variables, such as waist circumference, HCV RNA level, MELD score, HOMA2IR, etc., may be classified as corresponding to a patient who experienced fibrosis progression.

Once the classification module 310 classifies each of the patient variables and/or statistical measures in the training data set into first and second subsets corresponding to whether or not the patient experienced adverse health outcomes, the analysis module 320 may analyze the first and second subsets to generate a statistical model for determining a likelihood that a Hepatitis C patient will experience adverse health outcomes. For example, when the machine learning technique is random forests, the analysis module 320 may collect several representative samples of each of the first and second subsets of the training data. Using each representative sample, the analysis module 320 may generate a decision tree for determining a likelihood that a patient will experience adverse health outcomes. The analysis module 320 may then aggregate and/or combine each of the decisions trees to generate the statistical model, by for example averaging the likelihoods determined at each individual tree, calculating a weighted average, taking a majority vote, etc. In some embodiments, the analysis module 320 may also generate decision trees when the machine learning technique is boosting.

Each decision tree may include several nodes, branches, and leaves, where each node of the decision tree represents a test on a patient variable and/or statistical measure (e.g., is APRI acceleration greater than 0.03?), each branch represents the outcome of the test (e.g., the patient's APRI acceleration is greater than 0.03), and each leaf represents a likelihood that the patient will experience adverse health outcomes or a particular adverse health outcome based on the combined test outcomes for the branches which connect to the leaf.

For example, the analysis module 320 may generate a decision tree where a first node corresponds to whether the patient's mean MELD score is above seven. If the patient's mean MELD score is not above seven, a first branch may connect to a first leaf node which may indicate that the likelihood that the patient will experience adverse health outcomes is 0.2. If the patient's mean MELD score is above seven, a second branch may connect to a second node which corresponds to whether the patient's maximum HCV RNA level is above four million international units per milliliter (IU/mL).

If the patient's maximum HCV RNA level is above four million IU/mL, a third branch may connect to a second leaf node which may indicate that the likelihood that the patient will experience adverse health outcomes is 0.35. However, if the patient's maximum HCV RNA level is not above four million IU/mL, a fourth branch may connect to a third leaf node which may indicate that the likelihood that the patient will experience adverse health outcomes is 0.75. While the decision tree includes three leaf nodes and four branches, this is merely an example for ease of illustration only. Each decision tree may include any number of nodes, branches, and leaves, having any suitable number and/or types of tests on patient variables and/or statistical measures.

In any event, by combining and/or aggregating several decision trees as in random forests or boosting methods, the analysis module 320 may identify the patient variables and/or statistical measures which are the most important for determining the likelihood that a patient will experience adverse health outcomes. The most important patient variables and/or statistical measures are those that most frequently result in early splitting of the decision trees and are most indicative of whether or not a patient will experience adverse health outcomes. Referring to the example decision tree above, the mean MELD score may be more important than the maximum HCV RNA level, because the maximum HCV RNA level appears lower in the tree than the mean MELD score. Therefore, in this example, mean MELD score is the most important statistical measure.

By identifying the most important patient variables and/or statistical measures, the training module 160 may eliminate those patient variables and/or statistical measures which are the least important and may be misleading and/or random noise from the statistical model and when obtaining sets of training data in the future. In some embodiments, patient variables may be assigned weights according to their respective levels of importance. The analysis module 320 may then use the assigned weights when generating the statistical models. For example, mean MELD score may be weighted more heavily than HCV RNA level in the statistical model, such that the patient's MELD score may have a larger impact on her likelihood of experiencing adverse health outcomes than the patient's HCV RNA level. In another example, a patient variable and/or statistical measure which is the least important may be weighted by a factor of 0 or almost 0 to filter out the patient variable and/or statistical measure from the statistical model.

As mentioned above, the analysis module 320 may generate several statistical models each corresponding to a particular adverse health outcome. For example, the analysis module 320 may generate a first statistical model for determining a likelihood that a Hepatitis C patient will experience any adverse health outcomes, a second statistical model for determining a likelihood that a Hepatitis C patient will experience fibrosis progression, a third statistical model for determining a likelihood that a Hepatitis C patient will experience liver cancer, a fourth statistical model for determining a likelihood that a Hepatitis C patient will experience liver decompensation, etc.

Moreover, in some embodiments, the analysis module 320 may generate several statistical models each corresponding to a duration in which the patients are likely to experience any adverse health outcomes. For example, the analysis module 320 may generate a first statistical model for determining a likelihood that a Hepatitis C patient will experience adverse health outcomes within one year, a second statistical model for determining a likelihood that a Hepatitis C patient will experience adverse health outcomes within three years, a third statistical model for determining a likelihood that a Hepatitis C patient will experience adverse health outcomes within five years, etc.

Additionally, the analysis module 320 may generate a statistical model based on any combination of these classifications. For example, the analysis module 320 may generate a statistical model for determining a likelihood that a Hepatitis C patient will experience fibrosis progression within three years. In yet other embodiments, the analysis module 320 may create a single statistical model including several classifications, such as a statistical model for determining a likelihood that a Hepatitis C patient will experience adverse health outcomes, within one year, three years, and five years.

In any event, the statistical model generated by the analysis module 320 using random forests, boosting, or any other suitable machine learning technique such as logistic regression, naïve Bayes, etc., may be provided to the testing module 330. The testing module 330 may then utilize the statistical model to determine that a likelihood that a test patient having a set of test patient data will experience adverse health outcomes. The test patient may be a Hepatitis C patient where it is known whether she experienced adverse health outcomes. However, for purposes of testing, the testing module 330 may determine the likelihood that the test patient will experience adverse health outcomes by comparing the test patient's test patient data to the statistical model generated by the analysis module 320.

For example, the testing module 330 may traverse nodes from the aggregated and/or combined decision trees using the patient characteristics and/or statistical measures of the test patient data. In particular, a node of the aggregated and/or combined decision trees may correspond to whether the patient's mean Ishak score slope is above 0.5, for example. The testing module 330 may determine the test patient's mean Ishak score slope based on the test patient's Ishak score collected at several points in time. The testing module 330 may then follow a first branch of the node if the mean Ishak score slope is above 0.5, and a second branch of the node if the mean Ishak score slope is at or below 0.5. After traversing each of the nodes which correspond to the test patient's patient characteristics and/or statistical measures, the testing module 330 may reach a leaf which may indicate the likelihood that the test patient will experience adverse health outcomes. The likelihood determined by the testing module 330 may then be compared to the known patient health status.

In some embodiments, if the likelihood that the test patient will experience adverse health outcomes is above 0.5, and the known patient health status is that she did experience adverse health outcomes, the determination may be deemed correct. In other embodiments, the likelihood may have to be above 0.7 when the known patient health status is that she experienced adverse health outcomes, or some other predetermined threshold for the determined likelihood to be deemed correct.

Moreover, in some embodiments, when the testing module 330 is correct more than a predetermined threshold amount of the time, the statistical model may be presented to the disease progression assessment module 162. On the other hand, if the testing module 330 is not correct more than the threshold amount, the training module 160 may continue obtaining sets of training data for patients whose health status is known for further training.

Figure 4:
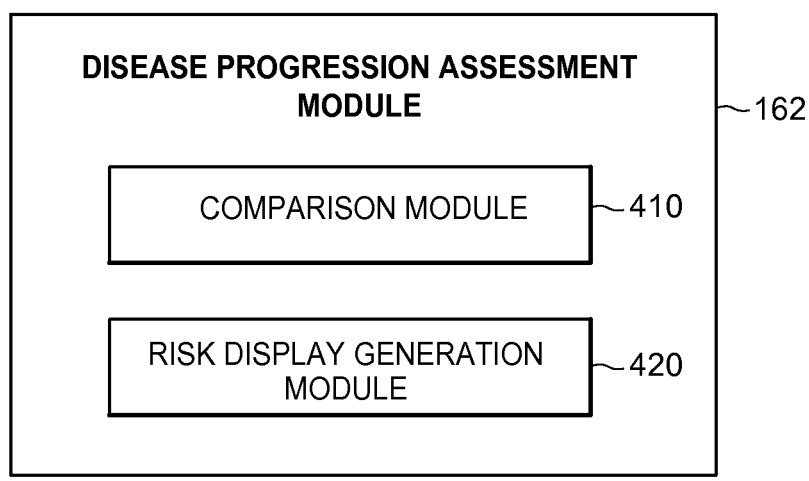
FIG. 4 depicts an exemplary disease progression assessment module in accordance with the presently described embodiments.

Once the statistical model has been adequately tested to verify its accuracy, the disease progression assessment module 162 may obtain the statistical model. Based on the statistical model, the disease progression assessment module 162 may determine the likelihood a Hepatitis C patient will experience adverse health outcomes, when the patient's health status is unknown. FIG. 4 is an exemplary block diagram of a disease progression assessment module 162. The disease progression assessment module 162 may include a comparison module 410 and a risk display generation module 420.

The comparison module 410 may obtain patient data for a Hepatitis C patient where it is unknown whether the patient will experience adverse health outcomes. The patient data may be collected at several points in time such as at baseline when the patient is first diagnosed with Hepatitis C, at a first follow-up visit six months later, and at a second follow-up visit one year after the first follow-up visit. In some embodiments, the patient data may be received from a network-enabled device of the patient's health care provider. Moreover, the patient data may include several patient characteristics, such as fixed characteristics, clinical variables, laboratory variables, and biopsy variables where each patient characteristic may collected at one or more of the points in time.

The comparison module 410 may calculate several statistical measures for each patient characteristic, such as a baseline, a mean, a maximum, a mean slope, a maximum slope, and an acceleration. Then the patient characteristics and/or statistical measures may be compared to the statistical model to determine a likelihood that the patient will experience adverse health outcomes. When the analysis module 320 generates several statistical models, the patient characteristics may be compared to each of the statistical models to determine likelihoods that the patient will experience fibrosis progression in one year, in three year, and in five years for example. In another example, the patient characteristics may be compared to each of the statistical models or a single statistical model for several classifications to determine a likelihood that the patient will experience any adverse health outcomes and a likelihood that the patient will require a liver transplant.

The risk display generation module 420 may receive the determined likelihood or likelihoods and generate a risk analysis display for the patient's health care provider to review. For example, the display may include indications of patient biographical information such as the patient's name, date of birth, address, etc. The display may also include indications of each of the likelihoods which may be represented as a probability (e.g., 0.6), a percentage (e.g., 80 percent), a category from a set of categories (e.g., "High Risk," "Medium Risk," or "Low Risk"), or in any other suitable manner. Additionally, each of the likelihoods may be displayed with a description of the classifications used to determine the likelihood, such as "Fibrosis Progression Risk (%) Within One Year" or "Liver Cancer Risk (%) Within Five Years." An example risk analysis display is described in more detail below with reference to FIG. 5.

Furthermore, when the patient's status becomes known (e.g., the patient experiences or does not experience an adverse health outcome after a predetermined threshold amount of time, such as five years), the patient data for the patient may be added to the training data set, and the statistical model may be updated accordingly.

FIG. 5 depicts a risk analysis page and/or screen 500 that the health risk assessment server 102 may transmit in various embodiments of the health risk assessment system 100. However, the screen depicted in FIG. 5 is merely an illustration of an exemplary embodiment. In some embodiments, the health risk assessment server 102 may transmit web pages.

In any event, referring to FIG. 2B, a user such as a health care provider may launch the client application 266 from one of the network-enabled devices 106-116 via any suitable manner, such as touch-selecting a client application icon (not shown) on the display 240 of a smart phone, double-clicking on the client application icon via a mouse of a computer and/or a trackpad of a laptop. After the user launches the client application 266, a home screen (not shown) of the client application 266 may be displayed to the user on one of the network-enabled devices 106-116.

The home screen (not shown) may include user controls for the health care provider to request to view a health risk assessment for a Hepatitis C patient. For example, the health care provider may be prompted to enter identification information for the Hepatitis C patient, such as the patient's name, social security number, phone number, address, date of birth, a patient identification number, etc. As a result, the client application 266 may display the most recent health risk assessment for the patient which may be received from the health risk assessment server 102 and/or may be stored in the client application 266.

In other embodiments, the home screen (not shown) and/or another screen of the client application may allow the health care provider to input patient data for a patient collected at one of the patient's follow-up visits. The patient data collected at the follow-up visit may be combined with patient data collected at baseline and/or previous follow-up visits and transmitted to the health risk assessment server 102. The client application 266 may then receive and display a health risk assessment generated in real-time or at least near real-time. In this manner, the health care provider may collect patient data and analyze updated risk for the patient all in the same follow-up visit.

In any event, the health risk assessment for the patient may be displayed on the risk analysis screen 500 as shown in FIG. 5. An authorized health care provider may view the risk analysis screen 500 upon receiving permission from the patient to access the patient's personal information. For example, health care providers may be required to login to a password-protected system to view the risk analysis screen 500. Moreover, a patient may be prompted to consent to having her health care provider access her personal information when the patients opt-in to the health risk assessment system or at the patient's first visit with the health care provider. In any event, the risk analysis screen 500 may include patient biographical information such as the patient's name, John Doe 502, and date of birth, Mar. 5, 1963 (reference 504). Additional biographical information may also be included such as the patient's address, phone number, the date in which the patient was first diagnosed with Hepatitis C, etc. Additionally, the risk analysis screen 500 may include a table 530 with likelihoods that the patient will experience certain types of adverse health outcomes within predetermined threshold amounts of time.

For example, the table 530 may include likelihoods that the patient will experience liver decompensation within one year, three years, and five years. Moreover, the table 530 may also include likelihoods that the patient will experience fibrosis progression within one year, three years, and five years. For example, the table 530 indicates that the likelihood that John Doe will experience liver decompensation within one year is 2.3 percent (reference 506), within three years is 5.7 percent (reference 508), and within five years is 10.3 percent (reference 510). Moreover, the table 530 also indicates that the likelihood that John Doe will experience fibrosis progression within one year is 8.2 percent (reference 512), within three years is 12.6 percent (reference 514), and within five years is 15.4 percent (reference 516).

While the likelihoods are represented in the risk analysis screen 500 as percentages, the likelihoods may be represented as probabilities (e.g., 0.6), categories from a set of categories (e.g., "High Risk," "Medium Risk," or "Low Risk"), or in any other suitable manner. Furthermore, while the likelihoods displayed in the risk analysis screen 500 correspond to liver decompensation and fibrosis progression within one, three, and five years, likelihoods may be displayed which correspond to any adverse health outcome, liver cancer, requiring a liver transplant, liver-related death, etc., and within any threshold amount of time, such as seven years, ten years, twenty years, etc.

In any event, John Doe's health care provider may review the risk analysis screen and may determine it is unlikely John Doe will experience liver decompensation or fibrosis progression within one year. However, the health care provider may also determine that the likelihoods increase significantly to 10.3 percent and 15.4 percent, respectively, within five years. As a result, John Doe's health care provider may recommend that Mr. Doe receive treatment due to his increased risk within five years.

Figure 6:
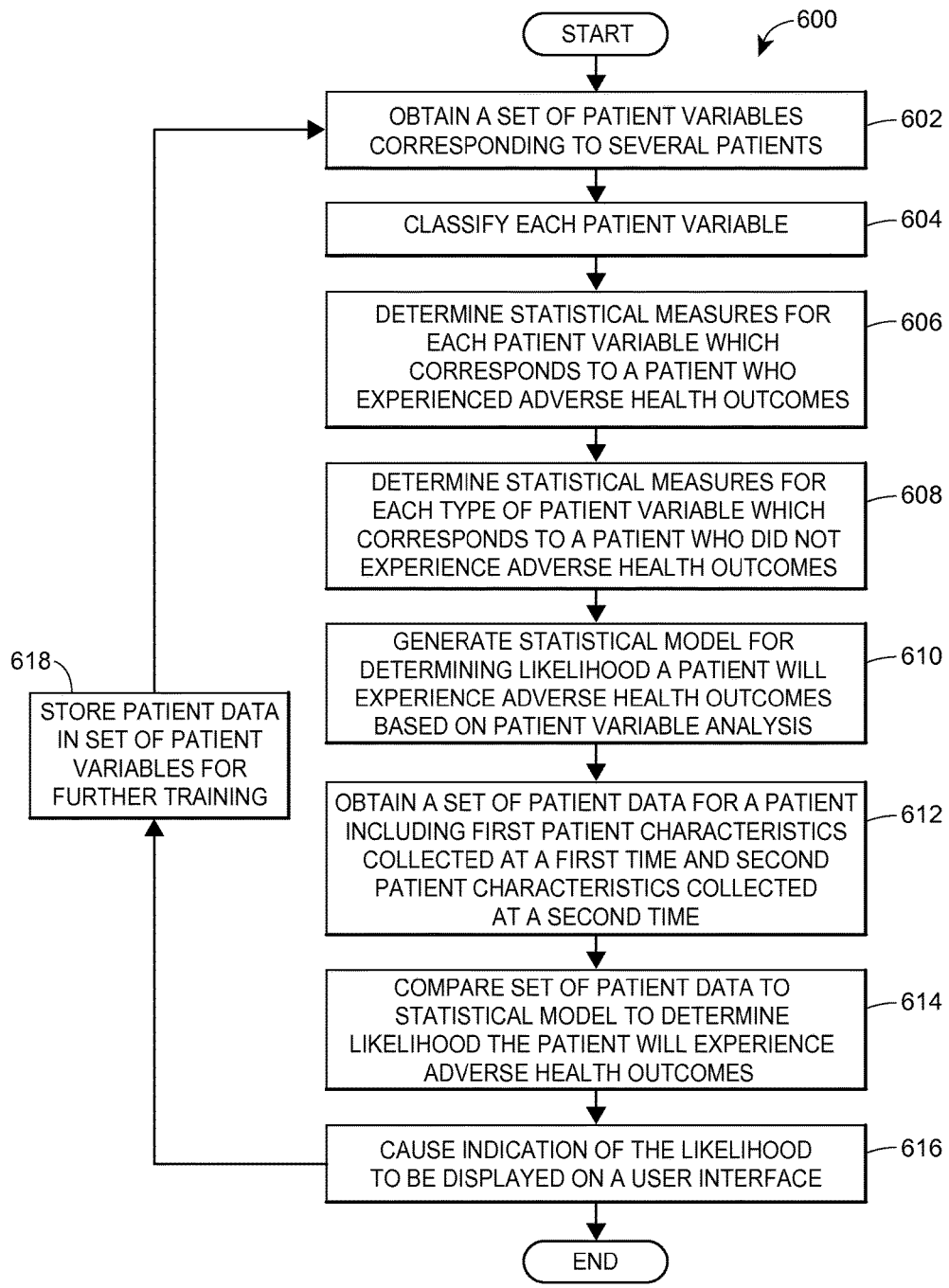
FIG. 6 illustrates a flow diagram representing an exemplary method for identifying Hepatitis C patients at high risk for disease progression in accordance with the presently described embodiments.

FIG. 6 depicts a flow diagram representing an exemplary method 600 for identifying Hepatitis C patients at high risk for disease progression. The method 600 may be executed on the health risk assessment server 102. In some embodiments, the method 600 may be implemented in a set of instructions stored on a non-transitory computer-readable memory and executable on one or more processors on the health risk assessment server 102. For example, the method 600 may be performed by the training module 160 and the disease progression assessment module 162 of FIG. 1.

At block 602, the training module 160 may obtain a set of training data including patient variables for Hepatitis C patients where it is known whether the patients experienced adverse health outcomes. The patient variables may include fixed characteristics, clinical variables, laboratory variables, and biopsy variables. Each of these patient variables may be obtained at several points in time for each patient, such as at baseline, at a follow-up visit four months later, and at another follow-up visit three years later.

The training module 160 may then classify the patient variables based on the health status of the patients associated with the patient variables (block 604). The classifications may include whether or not the associated patient experienced any adverse health outcomes, whether or not the associated patient experienced fibrosis progression, whether or not the associated patient experienced liver decompensation, whether or not the associated patient experienced any adverse outcomes within one year, whether or not the associated patient experienced any adverse outcomes within three years, etc.

For example, the patient variables may be classified into a first subset associated with a first set of Hepatitis C patients who did not experience any adverse health outcomes and a second subset associated with a second set of Hepatitis C patients who experienced adverse health outcomes.

For each patient variable in the first subset, the training module 160 may calculate several statistical measures, such as a baseline, a mean, a maximum, a mean slope, a maximum slope, and an acceleration (block 606). Additionally, for each patient variable in the second subset, the training module 160 may also calculate several statistical measures, such as a baseline, a mean, a maximum, a mean slope, a maximum slope, and an acceleration (block 608).

The statistical measures and/or patient variables in the first and second subsets may then be analyzed using various machine learning techniques to generate a statistical model for determining a likelihood that a patient will experience adverse health outcomes (block 610). In some embodiments, the statistical measures and/or patient variables may be analyzed using random forests or boosting methods. In other embodiments, the statistical measures and/or patient variables may be analyzed using logistic regression, naïve Bayes, or any other suitable machine learning techniques.

Moreover, the training module 160 may generate several statistical models for several classifications. For example, a first statistical model may be generated for determining a likelihood that a Hepatitis C patient will experience adverse health outcomes in one year, a second statistical model may be generated for determining a likelihood that a Hepatitis C patient will experience adverse health outcomes in two years, a third statistical model may be generated for determining a likelihood that a Hepatitis C patient will experience liver-related death, and a fourth statistical model may be generated for determining a likelihood that a Hepatitis C patient will experience liver decompensation in five years, etc. In any event, each statistical model may be a decision tree, a weighted decision tree, an aggregation and/or combination of several decision trees, a probability distribution, or any other suitable model for determining a likelihood that a Hepatitis C patient will experience adverse health outcomes based on data from other patients.

At block 612, a set of patient data for a Hepatitis C patient may be obtained. The patient data may be collected at several points in time such as at a first time at baseline when the patient is first diagnosed with Hepatitis C, at a second time during a first follow-up visit six months later, and at a third time during a second follow-up visit one year after the first follow-up visit. In some embodiments, the patient data may be received from a network-enabled device of the patient's health care provider. Moreover, the patient data may include several patient characteristics, such as fixed characteristics, clinical variables, laboratory variables, and biopsy variables where each patient characteristic may be collected at one or more of the points in time.

Then at block 614, the patient characteristics and/or statistical measures associated with the patient characteristics such as a mean, maximum, mean slope, acceleration, etc., may be compared to the statistical model to determine a likelihood that the patient will experience adverse health outcomes. For example, if the statistical model is a combination and/or aggregation of several decision trees, the disease progression assessment module 162 may traverse the nodes of the combined decision trees using the patient characteristics and/or statistical measures to determine the likelihood. If several statistical models are generated, the disease progression assessment module 162 may compare the patient characteristics and/or statistical measures to each of the statistical models to determine for example, a likelihood that the patient will experience adverse health outcomes in one year, a likelihood that the patient will experience adverse health outcomes in three years, a likelihood that the patient will experience adverse health outcomes in ten years, etc.

At block 616, the disease progression assessment module 162 may cause one or more indication(s) of the likelihood(s) that the patient will experience adverse health outcomes within one or more predetermined amount(s) of time to be displayed on a user interface of the health care provider's network-enabled device. For example, the network-enabled device may display the risk analysis screen 500 as shown in FIG. 5. In this manner, the patient's health care provider may view the likelihood(s) that the patient will experience adverse health outcomes and develop an appropriate treatment plan or course of treatment.

Furthermore, when the patient's health status becomes known (e.g., the patient experiences or does not experience an adverse health outcome after a predetermined threshold amount of time, such as five years) the patient data for the patient may be added to the training data set (block 618), and the statistical model may be updated accordingly.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as providing examples only and does not describe every possible embodiment, as describing every possible embodiment would be impractical, if not impossible. One could implement numerous alternate embodiments, using either current technology or technology developed after the filing date of this application.

We claim:

1. A computer-implemented method for identifying disease progression in Hepatitis C patients, the method executed by one or more processors programmed to perform the method, the method comprising:

obtaining, at one or more processors, a set of training data including a first subset having a first plurality of patient variables associated with a first set of patients having Hepatitis C who do not experience adverse health outcomes as a result of Hepatitis C and a second subset having a second plurality of patient variables associated with a second set of patients having Hepatitis C who do experience adverse health outcomes as a result of Hepatitis C;

receiving, at the one or more processors, a set of patient data for a patient collected over a period of time, wherein the set of patient data includes a first plurality of patient characteristics collected at a first time and a second plurality of patient characteristics collected at a second time, wherein at least some of the first and second plurality of patient characteristics are same patient characteristics collected at different points in time;

comparing, by the one or more processors, the set of patient data for the patient to the set of training data to determine a likelihood that the patient will experience adverse health outcomes as a result of Hepatitis C; and causing, by the one or more processors, an indication of the likelihood that the patient will experience adverse health outcomes to be displayed on a user interface of a network-enabled device of a health care provider, wherein the health care provider recommends a course of treatment to the patient according to the determined likelihood.

2. The computer-implemented method of claim 1, wherein comparing the set of patient data for the patient to the set of training data includes:

for each of the patient characteristics, determining a slope and an acceleration for the patient characteristic based on a difference between the first patient characteristic collected at the first time and the second patient characteristic collected at the second time; and comparing, by the one or more processors, the slope and the acceleration for each of the patient characteristics to the set of training data to determine the likelihood that the patient will experience adverse health outcomes.

3. The computer-implemented method of claim 1, wherein obtaining a set of training data includes:

classifying, by the one or more processors, each patient variable in the set of training data as corresponding to the first set of patients having Hepatitis C who do not experience adverse health outcomes as a result of Hepatitis C or the second set of patients having Hepatitis C who do experience adverse health outcomes as a result of Hepatitis C;

assigning, by the one or more processors, a weight to each patient variable in the set of training data based on a level of importance associated with an amount in which the patient variable is indicative of whether the patient having Hepatitis C will experience adverse health outcomes; and generating, by the one or more processors, a statistical model for determining whether the patient having Hepatitis C will experience adverse health outcomes based on the assigned weights and the classification for each patient variable.

4. The computer-implemented method of claim 1, further comprising:

receiving, by the one or more processors, an indication of whether the patient experiences an adverse health outcome as a result of Hepatitis C; and updating, by the one or more processors, the set of training data to include the set of patient data and the indication of whether the patient experiences the adverse health outcome.

5. The computer-implemented method of claim 1, wherein an adverse health outcome includes at least one of: (i) fibrosis progression, (ii) liver-related death, (iii) liver decompensation, (iv) liver cancer, or (v) the patient requires a liver transplant.

6. The computer-implemented method of claim 1, wherein the first and second plurality of patient characteristics includes fixed characteristics, clinical variables, laboratory variables, and biopsy variables, wherein the fixed characteristics and clinical variables include at least one of: (i) whether the patient has a history of alcohol and tobacco use, (ii) whether the patient has a history of diabetes, (iii) an estimated duration of hepatitis C infection, (iv) a body mass index, (v) a waist circumference, (vii) an amount of beta-blocker use, (viii) an amount of anti-hypertensive use, or (ix) an average amount of daily alcohol consumption.

7. The computer-implemented method of claim 1, wherein comparing the set of patient data for the patient to the set of training data to determine a likelihood that the patient will experience adverse health outcomes as a result of Hepatitis C includes:

comparing, by the one or more processors, the set of patient data for the patient to the set of training data to determine a plurality of likelihoods that the patient will experience adverse health outcomes as a result of Hepatitis C for a plurality of predetermined threshold amounts of time; and causing, by the one or more processors, indications of the plurality of likelihoods and the plurality of predetermined threshold amounts of time to be displayed on the user interface.

8. The computer-implemented method of claim 1, wherein comparing the set of patient data for the patient to the set of training data includes comparing, by the one or more processors, set of patient data for the patient to the set of training data using one or more machine learning techniques.

9. The computer-implemented method of claim 8, wherein the one or more machine learning techniques include at least one of random forests or boosting.

10. A computing device for identifying disease progression in Hepatitis C patients, the computing device comprising:

a communication network, one or more processors; and a non-transitory computer-readable memory coupled to the one or more processors and storing thereon instructions that, when executed by the one or more processors, cause the computing device to:

obtain a set of training data including a first subset having a first plurality of patient variables associated with a first set of patients having Hepatitis C who do not experience adverse health outcomes as a result of Hepatitis C and a second subset having a second plurality of patient variables associated with a second set of patients having Hepatitis C who do experience adverse health outcomes as a result of Hepatitis C;

receive, via the communication network, a set of patient data for a patient collected over a period of time, wherein the set of patient data includes a first plurality of patient characteristics collected at a first time and a second plurality of patient characteristics collected at a second time, wherein at least some of the first and second plurality of patient characteristics are same patient characteristics collected at different points in time;

compare the set of patient data for the patient to the set of training data to determine a likelihood that the patient will experience adverse health outcomes as a result of Hepatitis C; and cause, via the communication network, an indication of the likelihood that the patient will experience adverse health outcomes to be displayed on a user interface of a network-enabled device of a health care provider, wherein the health care provider recommends a course of treatment to the patient according to the determined likelihood.

11. The computing device of claim 10, wherein to compare the set of patient data for the patient to the set of training data, the instructions cause the computing device to:

for each of the patient characteristics, determine a slope and an acceleration for the patient characteristic based on a difference between the first patient characteristic collected at the first time and the second patient characteristic collected at the second time; and compare the slope and the acceleration for each of the patient characteristics to the set of training data to determine the likelihood that the patient will experience adverse health outcomes.

12. The computing device of claim 10, wherein to obtain a set of training data, the instructions cause the computing device to:

classify each patient variable in the set of training data as corresponding to the first set of patients having Hepatitis C who do not experience adverse health outcomes as a result of Hepatitis C or the second set of patients having Hepatitis C who do experience adverse health outcomes as a result of Hepatitis C;

assign a weight to each patient variable in the set of training data based on a level of importance associated with an amount in which the patient variable is indicative of whether the patient having Hepatitis C will experience adverse health outcomes; and generate a statistical model for determining whether the patient having Hepatitis C will experience adverse health outcomes based on the assigned weights and the classification for each patient variable.

13. The computing device of claim 10, wherein the instructions further cause the computing device to:

receive, via the communication network, an indication of whether the patient experiences an adverse health outcome as a result of Hepatitis C; and update the set of training data to include the set of patient data and the indication of whether the patient experiences the adverse health outcome.

14. The computing device of claim 10, wherein an adverse health outcome includes at least one of: (i) fibrosis progression, (ii) liver-related death, (iii) liver decompensation, (iv) liver cancer, or (v) the patient requires a liver transplant.

15. The computing device of claim 10, wherein the first and second plurality of patient characteristics includes fixed characteristics, clinical variables, laboratory variables, and biopsy variables, wherein the fixed characteristics and clinical variables include at least one of: (i) whether the patient has a history of alcohol and tobacco use, (ii) whether the patient has a history of diabetes, (iii) an estimated duration of hepatitis C infection, (iv) a body mass index, (v) a waist circumference, (vii) an amount of beta-blocker use, (viii) an amount of anti-hypertensive use, or (ix) an average amount of daily alcohol consumption.

16. The computing device of claim 10, wherein to compare the set of patient data for the patient to the set of training data to determine a likelihood that the patient will experience adverse health outcomes as a result of Hepatitis C, the instructions cause the computing device to:

compare the set of patient data for the patient to the set of training data to determine a plurality of likelihoods that the patient will experience adverse health outcomes as a result of Hepatitis C for a plurality of predetermined threshold amounts of time; and cause, via the communication network, indications of the plurality of likelihoods and the plurality of predetermined threshold amounts of time to be displayed on the user interface.

17. The computing device of claim 10, wherein to compare the set of patient data for the patient to the set of training data, the instructions cause the computing device to compare the set of patient data for the patient to the set of training data using one or more machine learning techniques.

18. The computing device of claim 17, wherein the one or more machine learning techniques include at least one of random forests or boosting.

* * * * *